United States Patent [19]

Nakayama et al.

[11] Patent Number: 5,214,034

[45] Date of Patent: May 25, 1993

[54] CATECHOL DERIVATIVES, AND PREVENTIVE AND REMEDIAL PREPARATIONS FOR REGRESSIVE DISORDERS IN THE CENTRAL NERVOUS SYSTEM CONTAINING THE SAME

[75] Inventors: Shigenobu Nakayama, Mihara; Fumiaki Ikeda, Takashi, both of Japan

[73] Assignee: Mitsui Toatsu Chemicals, Incorporated, Tokyo, Japan

[21] Appl. No.: 801,866

[22] Filed: Dec. 3, 1991

Related U.S. Application Data

[60] Division of Ser. No. 606,817, Oct. 31, 1990, Pat. No. 5,102,906, which is a division of Ser. No. 481,677, Feb. 20, 1990, Pat. No. 4,985,458, which is a continuation of Ser. No. 098,554, Sep. 21, 1987, abandoned.

[30] Foreign Application Priority Data

| Sep. 26, 1986 [JP] | Japan | 61-226135 |
| Dec. 22, 1986 [JP] | Japan | 61-303761 |
| Feb. 20, 1987 [JP] | Japan | 62-035697 |
| May 27, 1987 [JP] | Japan | 62-128444 |

[51] Int. Cl.$^5$ .................... A61K 31/60; A61K 31/235
[52] U.S. Cl. .................................... 514/159; 514/533
[58] Field of Search .................... 514/533, 159, 654

[56] References Cited

U.S. PATENT DOCUMENTS 4,559,328 12/1985 Smerbeck et al. .............. 514/159
4,608,391 8/1986 Ginos et al. .................... 514/654

FOREIGN PATENT DOCUMENTS 0185522 6/1986 European Pat. Off. .
916208 8/1954 Fed. Rep. of Germany .
2155985 5/1973 Fed. Rep. of Germany .
1256914 12/1971 United Kingdom .

OTHER PUBLICATIONS

Chemical Abstracts (104:219729u) 1986.
The Journal of Biological Chemistry, vol. 261, No. 13, May 5, 1986, pp. 6039–6047, Y. Furukawa, et al., "Catecholamines Induce an Increase in Nerve Growth Factor Content in the Medium of Mouse L-M Cells".
Journal of Neurochemistry, 1983, pp. 734–744, S. Furukawa, et al., "A Highly Sensitive Enzyme Imunoassay for Mouseβ Nerve Growth Factor".
Proc. Natl. Acad. Sci., vol. 83, Mar. 1986, pp. 1950–1954, M. Taniuchi, et al., "Nerve Growth Factor Receptor Molecules in Rat Brain".
The Journal of Biological Chemistry, vol. 261, No. 13, May 5, 1986, pp. 6039–6047, Y. Furukawa, et al., "Catecholamines Induce an Increase in Nerve Growth Factor Content in the Medium of Mouse L-M Cells".
Proc. Natl. Acad. Sci., vol. 83, Apr. 1986, pp. 2714–2718, D. L. Shelton, et al., "Studies on the Expression of the β Nerve Growth Factor (NGF) Gene in the Central Nervous System: Level and Regional Distribution of NGF mRNA Suggest That NGF . . . ".
Proc. Natl. Acad. Sci., vol. 83, Feb. 1986, pp. 817–821, S. R. Whittemore, et al., "Developmental and Regional Expression of β Nerve Growth Factor Messenger RNA and Protein in the Rat Central Nervous System".
Biochemical and Biophysical Research Communications, vol. 147, No. 3, Sep. 30, 1987, pp. 1048–1054, S. Furukawa, et al., "Regulation of Nerve Growth Factor Synthesis/Secretion By Catecholamine in Cultured Mouse Astrogial Cells".

(List continued on next page.)

Primary Examiner—Frederick E. Waddell
Assistant Examiner—Kevin F. Weddington
Attorney, Agent, or Firm—Oblon, Spivak, McClelland, Maier & Neustadt

[57] ABSTRACT

Catechol derivatives which relate to the production of nerve growth factor in particular tissues of brain are disclosed.

Methods for the synthesis, data on the physiological activity, and data on the toxicity of these derivatives as well as examples of preparation for their administration are also disclosed.

The disclosed derivatives provide preventive and remedial effect for regressive disorders in the central nervous system including senile dementia of Alzheimer type.

6 Claims, No Drawings

OTHER PUBLICATIONS

Biochemical and Biophysical Research Communications, vol. 136, No. 1, Apr. 14, 1986, pp. 57–63, S. Furukawa, et al., "Synthesis and Secretion of Nerve Growth Factor by Mouse Astroglial Cells in Culture".

FEBS, vol. 208, No. 2, Nov. 1986, pp. 258–262, Y. Furukawa, et al., "Aliphatic Side Chain of Catecholamine Potentiates the Stimulatory Effect of the Catechol part on the Synthesis of Nerve Growth Factor".

Proc. Natl. Acad. Sci., vol. 81, Dec. 1984, pp. 7951–7955, D. L. Shelton, et al., "Expression of the β-Nerve Growth Factor Gene Correlates with the Density of Sympathetic Innervation in Effector Organs".

Proc. Natl. Acad. Sci., vol. 80, Jun. 1983, pp. 3513–3516, S. Korsching, et al., "Nerve Growth Factor in Sympathetic Ganglia and Corresponding Target Organs of the Rat: Correlation with Density of Sympathetic Innervation".

Biochemical and Biophysical Research Communications, vol. 142, No. 2, Jan. 30, 1987, pp. 395–402, S. Furukawa, et al., "Synthesis/Secretion of Nerve Growth Factor is Associated with Cell Growth in Cultured Mouse Astroglial Cells".

The Journal of Biological Chemistry, vol. 259, No. 2, Jan. 25, 1984, pp. 1259–1264, Y. Furukawa, et al., "Nerve Growth Secreted by Mouse Heart Cells in Culture".

Physiological Reviews, vol. 60, No. 4, Oct. 1980, pp. 1284–1335, H. Thoenen, et al., "Physiology of Nerve Growth Factor".

The EMBO Journal, vol. 3, No. 13, 1984, pp. 1984, pp. 3183–3189, R. Heumann, et al., "Relationship Between Levels of Nerve Growth Factor (NGF) and Its Messenger RNA in Sympathetic Ganglia and Peripheral Target Tissues".

The EMBO Journal, vol. 4, No. 6, 1985, pp. 1389–1393, S. Korsching, et al., "Levels of Nerve Growth Factor and Its mRNA in the Central Nervous System of the Rat Correlate with Cholinergic Innervation".

Brain Research, 168, 1979, pp. 473–483, M. E. Schwab, et al., "Nerve Growth Factor (NGF) in the Rat CNS: Absence of Specific Retrograde Axonal Transport and Tyrosine Hydroxylase Induction in Locus Coeruleus and Substantia Nigra".

Brain Research, 300, 1984, pp. 33–39, M. Seiler, et al., "Specific Retrograde Transport of Nerve Growth Factor (NGF) from Neocortex to Nucleus Basalis in the Rat".

The Lancet, Jan. 22, 1977, pp. 189, E. K. Perry, et al., "Necropsy Evidence of Central Cholinergic Deficits in Senile Dementia".

P. J. Whitehouse, et al., "Alzheimer Disease: Evidence for Selective Loss of Cholinergic Neurons in the Nucleus Basalis", Annals of Neurology, vol. 10, No. 2, Aug. 1981, pp. 122–126.

Pharmacology Biochemistry & Behavior, vol. 18, 1983, pp. 973–981, C. Flicker, et al., "Behavioral and Neurochemical Effects Following Neurotoxic Lesions of a Major Cholinergic Imput to the Cerebral Cortex in the Rat".

Molecular Brain Research, 1, 1986, pp. 85–92, M. Goedert, et al., "Nerve Growth Factor mRNA in Peripheral and Central Rat Tissues and in the Human Central Nervous System: Lesion Effects in the Rat Brain and Levels in Alzheimer's Disease".

Ann. Rev. Biochem., 1982, pp. 845–868, B. A. Yankner, et al., "The Biology and Mechanism of Action of Nerve Growth Factor".

Natural Products and Biological Activities, A Naito Foundation Symposium, 1986, K. Hayashi, et al., "Synthesis and Secretion of Nerve Growth Factor by Mouse Heart Cells in Culture".

CAS Registry Handbook, 3 pages.

Ullmanns Encyclopadie der technischen Chemie, vol. 4, 1953, W. Foerst, "Brenzcatechin", p. 724.

CATECHOL DERIVATIVES, AND PREVENTIVE AND REMEDIAL PREPARATIONS FOR REGRESSIVE DISORDERS IN THE CENTRAL NERVOUS SYSTEM CONTAINING THE SAME

This is a divisional of application Ser. No. 07/606,817, filed Oct. 21, 1990, now U.S. Pat. No. 5,102,906, which is a divisional of Ser. No. 07/481,677, filed Feb. 20. 1990, now U.S. Pat. No. 4,985,458, which is a continuation of Ser. No. 07/098,554, filed on Sep. 21, 1987, now abandoned.

BACKGROUND OF THE INVENTION

1. Field of the Invention

The present invention relates to a series of chemical compounds which were found to have an activity for inducing the production and secretion of nerve growth factor (hereinafter abbreviated as NGF) in the local tissues of brain. The invention also relates to medicinal compositions containing these chemical compounds as effective ingredients.

The chemical compounds of this invention inhibit the progress of dysfunction of responsible nerves projecting into said local tissues by the activity of these compounds.

The chemical compounds further accelerate the repair of partly degenerated nerves and/or the reinnervation by intact neurons. The medicinal compositions of this invention containing aforesaid chemical compounds exert preventive and therapeutic effects on regressive disorders in the central nervous system including Senile Dementia of Alzheimer type (hereinafter abbreviated as SDAT) according to the action mechanism depending upon the above-mentioned "brain plasticity".

2. Description of the Prior Art

Basic and clinical researches have been promoted in order to establish early diagnosis and etiological therapy for various old age diseases with the advancement on average span of life in the world. The regressive disorders in the central nervous system is also one of the principal research subjects. SDAT, a typical disease in particular, is becomming an object of serious social concern as a result of a remarkable increase especially in advanced countries and a progressive and tragic course of the disease.

Particularly in recent years, many researchers and clinicians have investigated extensively and yet neither fundamental elucidation of the disease nor effective early diagnosis and therapy have been established. Many pathological findings, however, have been accumulated on the direct cause of failure in immediate memory and disorientation which are characteristic early symptoms of SDAT. According to these findings, the cause is a progressive degeneration in magnocellular cholinergic tracts projecting from basal forebrain into cerebral cortex and hiprocampus which are the centers of memory and learning, and an accompanied dysfunction in said responsible region. In addition, precursors in acetylcholine biosymthesis or inhibitors of choline esterase were actually administered to SDAT patients as an activation treatment for brain cholinergic neuron. Cases of partial improvement have been reported whereas generally no or only transient effect has been found as expected.

NGF has been the subjects of many researches since its discovery by R. Levi-Montalcini and S. Cohen et al. It has already been proved by several experiments in physiological chemistry that NGF is an essential factor for the peripheral nervous system relating to the differentiation and growth of sensory and sympathetic nerves in fetus and further to the survival and maintenance of functions in the sympathetic neurons of adult.

NGF, however, is a patent biologically active substance in an ultra trace amount. In spite of the long term researches, precise information have not been obtained on the tissue distribution and movement which directly prove vital functions. Most recently, development and improvement have been advanced on highly sensitive enzyme linked immunosorbent assay (hereinafter abbreviated as ELISA) on the active subunit of NGF, e.g. $\beta$-NGF (hereinafter simply referred to as NGF). Thus satisfactory sensitivity and specificity for the above examination have been attained [S. Furukawa et al, J. Neurochem., 40, 734–744 (1983); S. Korshing and H. Thoenen, Proc. Natl. Acad. Sci. USA, 80, 3513–3516 (1983)].

Besides NGF gene was cloned and sequenced. A method for the determination of messenger RNA (hereinafter abbreviated as m RNA) for $\beta$-NGF has been established by using its complemental DNA (hereinafter abbreviated as cDNA) as a probe [D. L. Shelton and L. F. Reichardt, Proc. Natl. Acad. Sci. USA, 81, 7951–7955 (1984); R. Heumann et al., EMBO J., 3, 3183–3189 (1984)].

By applying these procedures, a clear positive correlation has been proved between the sympathetic innervation in the peripheral nervous system and gene expression of NGF.

More surprisingly, NGF has also been detected in the central nervous system of rats, particularly in hippocampus, neocortex, and basal forebrain, e.g.,septum, olfactory bulb, diagonal band of Broca, and nucleus basalis magnocellularis. In addition, its mRNA content has been found at a high level in hippocampus and neocortex. On the other hand, the content in the septum of basal forebrain has been found at the same level as in other regions of brain where no NGF antigen was detected [S. Korshing et al., EMBO J., 4, 1389–1393 (1985)]. Thereafter the results have been successively traced by other research groups [D. L. Shelton and L. F. Reichardt, Proc. Natl. Acad. Sci. USA, 83, 2714–2718 (1986); S. R. Whittemore et al., Proc. Natl. Acad. Sci. USA, 83, 817–821 (1986)].

According to the aforesaid results, NGF gene is expressed not only in the peripheral nervous system, but in the central nervous system. Furthermore it was proved that NGF is produced and secreted in the neocortex and hippocampus, the centers of memory and learning, where the cholinergic tracts project from their origins in the base forebrain and then uptaken at the nerve endings and transported in the retrograde manner through axons to reach somata in origins. NGF has already been proved by a series of physiological experiments that it is an essential factor for the survival and maintenance of functions to the cholinergic tracts. Therefore, the result has demonstrated the assumption that NGF has a specific function as a "neurotropic factor" also in the central nervous system. Thereafter the experiment has been traced by several research groups and has also been proved by the investigation of NGF receptors and their distribution in brain.

The present inventors have investigated the function of NGF as the neurotropic factor in the central nervous system. As afore-mentioned in the prior art, the disorder in memory and learning which are the early symptoms of SDAT is directly caused by progressive degeneration of cholinergic tracts and consequent dysfunction of brain domains under their control.

The inventors, however, now stand on the point of view that the failure of production and secretion of NGF in particular regions of brain can be the truly fundamental cause of early symptoms in SDAT.

That is, conventional symptomatic trials against SDAT such as supplement and/or availability improvement therapies of acetylcholine have been made without any remarkable result. On the other hand, it is believed to be much effective if a functionally vicious cycle between responsible nerves and regions under its control could be broken by maintaining the production and secretion of NGF in cerebral cortex and hippocampus.

Besides the process for the preparation of human-type β-NGF in a large amount has already been developed by the gene-manipulation. Many pharmacological and pharmaceutical limitations, however, still exist on the supplemental therapy of NGF itself which is a protein having a molecular weight of above 10,000. Regarding the application for the central nervous system in particular, the prospect for its development has not yet been furnished.

BRIEF SUMMARY OF THE INVENTION

The present invention provides a catechol derivative capable of inducing the production and secretion ability of NGF in particular tissues in order to apply as a medicine for the substantially and effectively supplemental therapy of NGF.

The object of this invention is to increase the supplied quantity of NGF into the nerve-degenerating locus by ordinary administration of the catechol derivative and to recover the nervous function. The catechol derivative is administered as it is or as a modified compound in accordance with pharmacological and pharmaceutical considerations. In the regions under the control of specific nerves, the catechol derivative has activity for promoting the production and secretion of NGF which functions as "neurotropic factor" for the responsible nerves. In particular, the catechol derivative is expected to be satisfactory in the application to SDAT, a disorder in the central nervous system wherein fundamental therapy has not yet been established.

In the early onset stage of the symptoms, peripheral administration of the catechol derivative can enhance the production and secretion ability of NGF in the cerebral cortex and hippocampus regions of the central nervous system. The progress of characteristic degeneration in the responsible cholinergic neuron is thereby inhibited. The repair of damaged neurons and the reinnervation by surviving neurons are thus promoted.

Therefore this invention provides an epoch-making therapy according to a new action mechanism depending upon brain plasticity.

DETAILED DESCRIPTION OF THE PREFERRED EMBODIMENT

The present invention is a preventive and remedial preparation for regressive disorders in the central nervous system which comprises as an effective ingredient a catechol derivative having the formula (A):

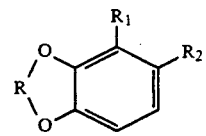

wherein R is two hydrogen atoms, two acyl groups, a —CO— group, —CO.CO— group, or —C(CH$_3$)$_2$— group, and wherein R$_1$ and R$_2$ are each independently a hydrogen atom or lower alkyl group.

Among these derivatives for use in the medicinal compositions, the below described derivative is a novel compound which has not yet been known.

That is, a catechol derivative having the formula (B):

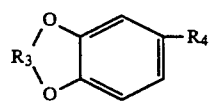

wherein R$_3$ is two acyl groups, a —CO— group, —CO.CO— group or —C(CH$_3$)$_2$— group, and R$_4$ is a lower alkyl group, and wherein excluding when R$_3$ is acetyl group and R$_4$ is methyl group and when R$_3$ is —CO.CO— group and R$_4$ is methyl group.

More practical illustration of the derivative is:

(1) A catechol derivative having the formula (C):

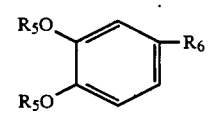

wherein R$_5$ is an acyl group and R$_6$ is a lower alkyl group, and wherein excluding when R$_5$ is an acetyl group and R$_6$ is a methyl group, (2) a catechol derivative having the formula (D):

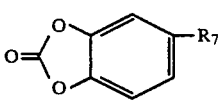

wherein R$_7$ is a lower alkyl group, (3) a catechol derivative having the formula (E):

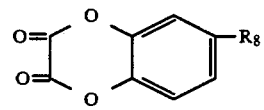

wherein R$_8$ is a lower alkyl group and wherein excluding when R$_8$ is a methyl group, and (4) a catechol derivative having the formula (F):

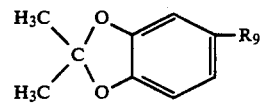

wherein R$_9$ is a lower alkyl group.

At the first step, neurotransmitters and agonists of their receptors, neuromodulators, etc. and their structurally related compounds were selected in order to search the active derivative of this invention. Typical compounds were selected from those exhibiting the activity for accelerating the production and secretion of NGF in the screening system in vitro using cultured cells. In the experiments in vivo using rats, these typical compounds have induced the production and secretion of NGF in the particular regions of brain even by the peripheral administration. Furhtermore, these compounds have been confirmed to remarkably improve behavioral pharmacological parameters. supposing anti-SDAT activity. Thus the present invention has been achieved.

That is, in the peripheral nervous system, a positive correlation has been observed between NGF-gene expression in the specific tissue and norepinephrine content, e.g. level of sympathetic innervation [D. L. Shelton and L. F. Reichardt, Proc. Natl. Acad: Sci USA, 81, 7951-7955 (1984)]. Norepinephrine itself, a neurotransmitter secreted from nerve endings, was possible to be a positive effector for the NGF-gene expression, and such suggestion led to the present invention.

Actually Furukawa et al. have reported that L-M-cells, e.g. cultured cells derived from the peripheral tissue, were accelerated the production amount of NGF by some compounds of catecholamines.

The present inventors have also identified the fact by a similar experimental system. Furthermore, it has been surprisingly found that the total structure of catecholamines are not needed for exerting the acceleration effect, but catechol ring (1,2-dihydroxybenzene) is essential. It has also been found that the alkyl substituents at 3- and/or 4-positions on the catechol ring determine the activity of the catechol derivative. In addition to such a relatively simple catechol derivative, its hydroxyl groups in 1 and 2 positions were chemically modified in accordance with pharmaceutical and toxicological considerations. The derivative thus obtained has also been proved to have similar activity.

More surprisingly, any of such derivative has also exerted activity for promoting the production and secretion of NGF in the culture systems of astroglial cells derived from the brain. Moreover the activity of such derivative has been remarkable as compared with that of catecholamines. The typical catechol derivative has further accelerated by the peripheral administration the production of NGF in the central nervous system of rats, particularly in the cerebral cortex and hippocampus. The examination on behavioral pharmacology has also revealed that the derivative has activity for recovering model animals disordered in the memory and learning functions from their damaged conditions.

In the catechol derivative of this invention having the formula (A) to (F), the acyl group is acetyl group, propionyl group, butyryl group or isobutyryl group etc. and the lower alkyl group is methyl group, ethyl group, propyl group, isopropyl group, butyl group or isobutyl group etc.

The catechol derivative which may be used in this invention is prepared by the below described processes.

I. Catechol derivative having the formula (C)

(a) When $R_6$ is methyl group:

(1) A method for reacting homocatechol with a corresponding lower fatty acid or its anhydride in the presence of an acid catalyst including mineral acids such as sulfuric acid, hydrogen halide etc., Lewis acids such as anhydrous aluminium chloride, zinc chloride, iron chloride, titanium tetrachloride, tin tetrachloride boron fluoride etc., and the like.

(2) A method for reacting homocatechol with a lower fatty acid anhydride at an elevated temperature.

(3) A method for reacting homocatechol with a lower fatty acid or its anhydride in the presence of a base including alkali metal hydroxides such as sodium hydroxide, potassium hydroxide etc., alkali metal carbonates such as sodium carbonate, sodium hydrogen carbonate, potassium carbonate potassium hydrogen carbonate etc., alkali metal salts of fatty acid such as sodium acetate etc. and organic amines such as triethylamine, pyridine etc.

(4) A method for reacting homocatechol with a lower fatty acid chloride in the presence of a base illustrated in (3).

(b) When $R_6$ is other than methyl group:

(1) The compound having the below described formula (G) is hydrogenated in the presence of a catalyst such as Pd/c etc. to give an intermediate having the formula (H). The methyl groups of the intermediate are removed by subjecting to a heat treatment in a solvent such as acetic acid, acetic anhydride etc. in the presence of hydrogen iodide, hydrogen bromide, hydrogen chloride etc. The resulting 4-alkylcatechol is reacted by the various methods illustrated in (a) above, and the derivative of this invention having the formula (C) is obtained.

Formula (G):

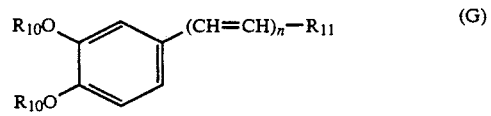

wherein $R_{10}$ is an acyl group, $R_{11}$ is a hydrogen atom or a lower alkyl group and n is an integer of 1 or 2.

Formula (H):

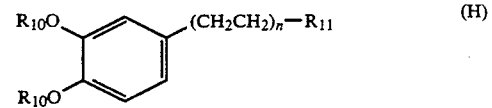

wherein $R_{10}$, $R_{11}$ and n are the same as above. (2) Veratrols are reacted with a fatty acid anhydride or a fatty acid halide such as fatty acid chloride etc. in the presence of a catalyst including iodine, anhydrous aluminium chloride, zinc chloride, iron chloride, titanium tetrachloride, tin tetrachloride, boron fluoride etc. The resulting 4-acylveratroles are subjected to hydrogenation and dehydration in the presence of a metal catalyst such as $LiAlH_4$, $NaBH_4$, Pd/C etc., to Clemmensen reduction, or to Wolff-Kishner reduction, in order to obtain corresponding 4-alkylveratroles. The methyl groups of 4-alkylveratroles are removed by subjecting to a heat treatment in a solvent such as acetic acid, acetic anhydride etc. in the presence of hydrogen iodide, hydrogen bromide, hydrogen chloride etc. 4-alkylcatechols thus obtained are reacted by the various methods illustrated in (a) above, and the derivative of this invention having the formula (C) is obtained.

(3) Catechol is reacted with a fatty acid halide such as fatty acid chloride, fatty acid bromide etc. in the presence of a Lewis acids such as anhydrous aluminium chloride, zinc chloride, iron chloride, titanium tetrachloride, tin tetrachloride, boron fluoride etc. Corresponding 4-acylcatechols thus obtained is reduced by the method illustrated in (2) to give corresponding 4-alkylcatechols. The resulting 4-alkylcatechols are converted to the derivative of this invention having the formula (C) by the various methods illustrated in (a).

By the various methods mentioned above, the catechol derivative having the formula (C) can be prepared.

II. Catechol derivative having the formula (D).

The catechol derivative having the formula (D) can be prepared by reacting a 4-alkylcatechol derivative obtained by the above method I (b) with phosgen or diethyl carbonate in the presence of a base. The base which may be employed in this method include, for example, inorganic bases such as sodium hydroxide, potassium hydroxide etc. and organic bases such as triethylamine, pyridine etc. The reaction is carried out without solvent or in an organic solvent such as benzene, tertrahydrofuran etc. at the room temperature or under heated conditions.

III. Catechol derivative having the formula (E).

The catechol derivative having the formula (E) can be prepared by reacting a 4-alkylcatechol derivative obtained by the above method I (b) with oxalyl chloride in an inert solvent in the presence or absence of a base. The examples of the solvent which may be used in this method include, aromatic solvents such as benzene, toluene, xylene, chlorobenzene, nitrobenzene etc., ether solvents such as dioxane, tetrahydrofuran, ethyl ether etc., and mixtures of these solvents. The examples of the base which may be used in this method are the same as used in II. The reaction is carried out at the room temperature or under heated conditions.

IV. Catechol derivative having the formula (F)

The catechol derivative having the formula (F) can be prepared by reacting a 4-alkylcatechol derivative obtained by the above method I(b) with acetone without solvent or in an inert solvent in the presence of an acid catalyst under continuously removing the water generated as a by-product.

Examples of the solvent which may be used in this method include alicyclic solvents such as cyclopentane, cyclohexane etc. and aromatic solvents such as benzene, toluene, xylene, chlorobenzene, nitrobenzene etc.

Examples of the acid catalyst which may be used in this method include mineral acids such as sulfuric acid, phosphoric acid, hydrogen halide etc., Lewis acids such as anhydrous aluminium chloride, zinc chloride, iron chloride, titanium tetrachloride, tin tetrachloride, boron fluoride etc., organic sulfonic acids such as p-toluenesulfonic acid, methanesulfonic acid, dodecylsulfonic acid etc., organotin compounds such as dibutyltin oxide, dibutyltin dilaurate, dimethyltin dichloride etc., metal alkoxides such as titanium isopropoxide, cation exchange resin and the like.

The derivative of this invention can be prepared by various methods illustrated above. When the derivative of this invention is used as the preventive and remedial preparation for the regressive disorders in the central nervous system, particularly for SDAT, dose and dosage form depend upon the properties of the derivative and symptoms of the patient. For example, esterified 4-n-propylcatechol can be administered a dosage of 50-500 mg per adult per day several times with an interval of few days orally as tablets, granules, powders, suspensions etc. or non-orally as supositories, injections, isotonic solutions for infusion etc. As a general prescription in particular, 50-500 mg of primary medicine is dissolved in 10 ml of oil such as cotton seed oil, corn oil, peanut oil, olive oil etc. in order to prepare non-aqueous injections. This prescription may be further added with 10 ml of water in the presence of a surfactant such as HCO-60 in a final concentration of about 5% as HCO-60 and emulsified to prepare aqueous injections. Besides tablets may be prepared as follows. With 50 mg of main medicine, crystalline cellulose (150, 120 mg each) and light anhydrous silicic acid (3, 30 mg each) are mixed as adsorbent, corn starch (94, 97 mg each) is further added as a excipient, and finally magnesium stearate (3 mg) is incorporated to prepare a tablet of 500 mg.

Biological and pharmacological actions will hereinafter be described in detail on the derivative of this invention having the formula (A) to (F).

Promoting action for the production and secretion of NGF on L-M cells of mouse

The mouse fibroblasts cell line, e.g. L-M cells (ATCC, CCL 1.2), has been found to be capable of growing in the absence of serum, and producing and secreting NGF in the medium. Catecholamines have also been found in a relatively high concentration to accelerate these functions without being mediated by adrenergic receptors [Y. Furukawa et al., J. Biol. Chem., 261, 6039-6047 (1986)].

According to similar systems, the activity of a series of the derivative in this invention having the formula (A) wherein R is two hydrogen atoms has been examined on various combinations of $R_1$ and $R_2$ alkyl groups. Any derivative tested has exerted activity as illustrated in Table 1.

Besides l-epinephrine employed as a typical compound of the catecholamines has shown an activity of $6.29 \pm 0.11$ at a concentration of 0.05 mM, and $13.99 \pm 0.83$ at 0.15 mM.

As a result of these experiments, the difference in the positions of substituent $R_1$ and $R_2$ has been found indefinite. The derivative wherein $R_1$ or $R_2$ is a n-alkyl group having 2 to 5 carbon atoms, the combination of $R_1$ and $R_2$ is less bulky, and favorably $R_1$ or $R_2$ is a hydrogen atom, has been found effective. Such derivative has also been found to exhibit the efficacy almost equal to or superior to that of the effective catecholamines in a lower concentration than the latter. Besides the derivative having smaller substituents decreased its activity in higher concentrations whereas no tendency was found on larger substituents. The derivative which exerted a high activity was different from catecholamines and unknown on the existence of activity for the adrenergic neurotransmitters.

Therefore it was considered advantageous to apply the derivative of this invention to clinical uses, and the derivative was intended to undergo a search in a higher-order examination.

The compound having a high activity in Table 1, that is, the catechol derivative having a n-alkyl group in the 3 or 4 position on the ring has been observed an acute cell toxicity in higher concentrations. The toxicity was considered the result of two hydroxyl groups in the catechol structure. Then the hydroxyl groups were esterified or etherified and the resulting derivative was examined the effect on the activity for the production and secretion of NGF. The results obtained are illustrated in Table 2.

In this experiment, the etherified derivative obtained by converting one or both hydroxyl groups to methoxy groups exhibited no activity at all. On the other hand, the esterified derivative in the second group reduced its effect by about a half in a short-term cultivation and yet the activity lowering was inhibited in higher concentrations. Furthermore the activity was found to recover to almost the same level in a long-term cultivation. Besides the etherified derivative (F) was found to partly reserve its efficacy. Therefore these chemical modifications were considered as a potent countermeasure for the utmost inhibition of acute phase toxicity in the administration for living bodies. Such type of esterified derivative and a part of etherified derivative were also intended to undergo a search in a higher-order examination.

Method of experiment

The experiment was performed according to the procedures of Y. Furukawa et al. which is described in J. Bis Chem., 261, 6039–6047 (1986).

Mouse L-M cells were precultured in Medium 199 (a product of Gibco Co.) supplemented with 0.5% peptone, and then innoculated in a 24-well cultivation plate having a well surface area of 2.1 cm$^2$ (a product of Falcon Co.) at a cell density of about $3 \times 10^4$ cells/well. The medium was cultured for 3 days at a temperature of 37° C. After completing the confluency (about $10^6$ cells/well), the medium was changed to Medium 199 (0.5 ml/well) containing 0.5% bovine serum albumin (Fraction V, a product of Armour Co.). The sample of the derivative is contained in the medium at a prescribed concentration as illustrated in the Tables. NGF concentration in the medium after cultivating for 24 hours was determined according to high sensitivity ELISA (S. Furukawa et al., J. Neurachem., 40, 734–744 (1983)]. Data are expressed as fold increase in NGF content of the medium over that cultivated in the absence of the derivative to be tested. Lower detection limit of ELISA is 0.25 pg/ml and the NGF content of control medium is normally 50–200 pg/0.5 ml/well. Data was presented as means ±SE of four determinations.

TABLE-1

| Derivative (A) R = Two H | | Concentration | Ratio of |
|---|---|---|---|
| $R_1$ | $R_2$ | (mM) | NGF increase |
| Control | | | 1.00 ± 0.06 |
| H | H | 0.03 | 1.03 ± 0.04 |
| | | 0.10 | 1.81 ± 0.09 |
| 1st Group | | | |
| Methyl | H | 0.03 | 8.34 ± 0.82 |
| | | 0.10 | 3.92 ± 1.23 |
| H | Methyl | 0.03 | 8.91 ± 0.43 |
| | | 0.10 | 2.36 ± 1.90 |
| 2nd Group | | | |
| Methyl | Methyl | 0.03 | 2.86 ± 0.12 |
| | | 0.10 | 3.11 ± 0.22 |
| Ethyl | H | 0.03 | 9.76 ± 1.40 |
| | | 0.10 | 11.65 ± 2.13 |
| H | Ethyl | 0.03 | 10.03 ± 0.97 |
| | | 0.10 | 12.13 ± 1.09 |
| 3rd Group | | | |
| Ethyl | Methyl | 0.03 | 6.62 ± 0.29 |
| | | 0.10 | 2.98 ± 0.55 |
| Methyl | Ethyl | 0.03 | 6.31 ± 0.39 |
| | | 0.10 | 3.19 ± 0.73 |
| n-Propyl | H | 0.03 | 9.81 ± 0.92 |
| | | 0.10 | 16.30 ± 2.04 |
| H | n-propyl | 0.03 | 10.14 ± 1.14 |
| | | 0.10 | 17.07 ± 2.70 |
| H | Isopropyl | 0.03 | 6.17 ± 0.44 |
| | | 0.10 | 5.90 ± 0.41 |
| 4th Group | | | |
| Ethyl | Ethyl | 0.03 | 3.01 ± 0.20 |
| | | 0.10 | 3.24 ± 0.19 |
| n-Propyl | Methyl | 0.03 | 6.09 ± 0.65 |
| | | 0.10 | 6.98 ± 0.51 |
| Methyl | n-Propyl | 0.03 | 6.34 ± 0.46 |
| | | 0.10 | 7.25 ± 0.32 |
| n-Butyl | H | 0.03 | 8.33 ± 0.52 |
| H | n-Butyl | 0.10 | 13.96 ± 1.33 |
| | | 0.03 | 8.21 ± 1.10 |
| H | sec-Butyl | 0.10 | 14.65 ± 1.87 |
| | | 0.03 | 9.23 ± 1.41 |
| H | tert-Butyl | 0.10 | 13.27 ± 1.96 |
| | | 0.03 | 3.45 ± 0.35 |
| | | 0.10 | 4.29 ± 0.33 |
| 5th Group | | | |
| Ethyl | Methyl | 0.03 | 5.41 ± 0.23 |
| | | 0.10 | 5.02 ± 0.49 |
| Methyl | Ethyl | 0.03 | 5.39 ± 0.31 |
| | | 0.10 | 5.22 ± 0.27 |
| n-Butyl | Methyl | 0.03 | 6.33 ± 0.75 |
| | | 0.10 | 6.90 ± 0.62 |
| Methyl | n-Butyl | 0.03 | 6.87 ± 0.60 |
| | | 0.10 | 7.73 ± 0.53 |
| Methyl | sec-Butyl | 0.03 | 6.74 ± 0.25 |
| | | 0.10 | 7.00 ± 0.76 |
| Methyl | tert-Butyl | 0.03 | 2.82 ± 0.14 |
| | | 0.10 | 3.65 ± 0.39 |
| n-Pentyl | H | 0.03 | 5.26 ± 0.43 |
| | | 0.10 | 9.95 ± 0.98 |
| H | n-Pentyl | 0.03 | 6.37 ± 0.25 |
| | | 0.10 | 10.24 ± 0.71 |

TABLE-2

| Derivative (A) | Concentration (mM) | Ratio of NGF increase* | |
|---|---|---|---|
| | | 24-hr culture | 48-hr culture |
| Control | | 1.00 ± 0.07 | 1.21 ± 0.06 |
| Catechol | 0.03 | 1.15 ± 0.04 | 1.31 ± 0.09 |
| | 0.15 | 1.93 ± 0.12 | 1.79 ± 0.20 |
| 4-Methylcatechol | 0.03 | 8.77 ± 0.66 | 9.21 ± 0.69 |
| | 0.15 | 2.87 ± 0.54 | 2.49 ± 0.88 |
| 1st Group | | | |
| 4-Methylguaiacol | 0.03 | 1.09 ± 0.06 | 1.10 ± 0.07 |
| | 0.15 | 1.03 ± 0.05 | 1.00 ± 0.09 |
| R = Two methyl, $R_1$ = H, $R_2$ = Methyl | 0.03 | 1.04 ± 0.07 | 1.03 ± 0.07 |
| | 0.15 | 0.98 ± 0.06 | 0.98 ± 0.02 |
| R = -C(CH$_3$)$_2$-, $R_1$ = H, $R_2$ = Methyl | 0.03 | 1.35 ± 0.12 | 4.33 ± 1.05 |
| | 0.15 | 1.22 ± 0.08 | 3.86 ± 0.84 |
| 2nd Group | | | |
| R = Two acetyl | 0.03 | 4.92 ± 0.94 | 7.71 ± 0.86 |
| $R_1$ = H, $R_2$ = Methyl | 0.15 | 4.21 ± 0.40 | 6.27 ± 0.75 |
| R = -CO-, $R_1$ = H $R_2$ = Methyl | 0.03 | 4.39 ± 0.62 | 7.54 ± 0.72 |
| | 0.15 | 4.82 ± 0.55 | 6.99 ± 0.52 |
| R = -CO.CO-, $R_1$ = H $R_2$ = Methyl | 0.03 | 4.24 ± 0.58 | 7.60 ± 0.43 |
| | 0.15 | 4.62 ± 0.61 | 7.03 ± 0.69 |

Note: *Fold increase over control of 2-hr culture.

Promoting activity for the production and secretion of NGF in brain astroglial cells of mouse The derivative which promoted the production and secretion of NGF in the mouse cell line derived from peripheral tissue was further searched its promoting activity by astroglial cells which were considered as a major source of NGF in the central nervous system.

The derivative being suitable for the object of this invention wa thus selected.

It has already been elucidated that astroglial cells produce and secrete NGF in a different strength of activity depending upon their growth phase. They secrete only at a very low level of a few pg,$10^6$ cells/day in the quiescent stage. On the other hand, they secret at a high high level of 200-300 pg/$10^6$ cells/day in the growing stage when induced from the quiescent stage in the presence of 10% of fetal calf serum [S. Furukawa et al., Biochem. Biophys. Res. Commun., 136, 57-63 (1986)].

The activity of a series of the derivative in this invention having the formula (A) wherein R is two hydrogen atoms has been examined on various combinations of $R_1$ and $R_2$ alkyl groups. Any derivative tested has exerted activity as illustrated in Table 3. Besides the fetal calf serum employed as a control has shown an activity of 45.58±5.52, while l-epenephrine has shown an activity of 8.62±1.21 at the concentration of 0.10 mM, and 14.55±2.67 at 0.25 mM.

Structure activity correlations are very similar to those of L-M cells and the difference in the positions of substituent $R_1$ and $R_2$ has been found indefinite. The derivative wherein $R_1$ or $R_2$ is a n-alkyl group having 2 to 5 carbon atoms, the combination of $R_1$ and $R_2$ is less bulky, and favorably $R_1$ or $R_2$ is a hydrogen atom has been found to exert much higher activity than that of fetal calf serum. It was noteworthy that the activity of catecholamines was remarkably weaker than that of the derivative of this invention contrary to the effect on L-M cells.

Hydroxy-substituted derivative of catechol has been examined its function and the results are illustrated in Table 4. Also in this case, the esterified derivative inhibited the activity reduction due to cell toxicity in the acute phase and has been found to exert almost same level of activity in a long-term cultivation as compared with the derivative having free hydroxyl groups.

Astroglial cells are considered as major cells for the production and secretion of NGF in the brain. Calculating from gene-expression frequency in the total brain, astroglial cells are considered physiologically in the quiescent stage [D. L. Shelton and L. F. Reichardt, Proc. Natl. Acad. Sci. USA, 83, 2714-2718 (1986)].

The catechol derivative having lower n-alkyl groups at the 3 and/or 4 positions has induced a remarkable activity for producing and secreting NGF to the astroglial cells in the quiescent stage. Therefore the derivative including the esterified catechol derivative is expected to remarkably activate the NGF production system in the brain by administration to the living bodies.

Method of experiment

The experiment was performed by inducing the astroglial cells from mouse forebrain to culture system according to the procedures of S. Furukawa et al. which is described in Biochem. Biophys. Res. Commun., 136, 57-63 (1986).

That is, forebrains of 8-day old mice were dissected out and cut into small pieces. The pieces were washed with calcium- and magnesium-free phosphate-buffered saline (hereinafter abbreviated as PBS), treated with 0.25% trypsin containing PBS at 37° C. for 30 minutes and triturated with a Pasteur pipet to give a suspension. Cells and cell clamps were recovered by centrifugation at 200 xg for 5 minutes. They were cultured in Dulbecco modified Eagle's medium (a product of Gibco Co. hereinafter abbreviated as DMEM) containing 10% of fetal calf serum, 50 μ units/ml of penicillin, and 50 μg/ml of streptomycin, for 10 to 14 days with medium changes every 3 days. After completing confluency, the cells were dissociated by trypsin treatment and recultured in new culture flasks. This procedure was repeated further twice and more. The culture became a uniform cell cluster. The cell cluster for use in this invention can be stained not less than 97% in accordance with PAP staining method (peroxidase/antioxidase staining method) using anti-human glial fibrillar acidic protein (GFAP) rabbit antiserum. The cells will hereinafter be referred to as astroglial cells.

Astroglial cells were innoculated in 24-well plates having a well surface area of 2.1 cm$^2$ (a product of Falcon Co.) at a cell density of about $3 \times 10^4$ cells/well and cultured for 3 days in DMEM . medium supplemented with 10% of fetal calf serum. After completing confluency about $10^7$ cells/well), the medium was changed to DMEM medium (0.5 ml/well) supplemented with 0.5% of bovine serum albumin ((fraction V) and cultured for 3 days. The culture was further continued with medium changes every 3 days. After cells were practically synchronized in the quiescent stage, the medium was changed to 0.5 ml of the medium supplemented with 0.5% of bovine serum albumin and containing a prescribed concentration of test sample as illustrated in Tables. NGF in the medium after cultivating for 24 hours was determined by the ELISA as mentioned above. Data are expressed as fold increase in NGF content over that in the absence of the test sample. Lower detection limit of the ELISA is 0.25 pg/ml and the NGF content of control medium was normally 1-10 pg/0.5 ml/well. Data are presented as means ±SE of four determinations.

TABLE-3

| Derivative | | Concentration (mM) | Ratio of NGF increase |
|---|---|---|---|
| R = Two H | | | |
| $R_1$ | $R_2$ | 0.10 | 2.51 ± 0.07 |
| Control | | | |
| H | H | 0.25 | 1.92 ± 0.09 |
| 1st Group | | | |
| Methyl | H | 0.10 | 76.27 ± 6.34 |
| | | 0.25 | 5.02 ± 1.98 |
| H | Methyl | 0.10 | 80.75 ± 4.21 |
| | | 0.25 | 4.89 ± 1.37 |
| 2nd Group | | | |
| Methyl | Methyl | 0.10 | 4.97 ± 1.07 |
| | | 0.25 | 8.30 ± 1.14 |
| Ethyl | H | 0.10 | 46.25 ± 3.97 |
| | | 0.25 | 62.75 ± 4.42 |
| H | Ethyl | 0.10 | 55.21 ± 3.24 |
| | | 0.25 | 64.65 ± 4.26 |
| 3rd Group | | | |
| Methyl | Ethyl | 0.10 | 50.26 ± 6.27 |
| | | 0.25 | 26.24 ± 2.60 |
| n-Propyl | H | 0.10 | 72.93 ± 7.09 |
| | | 0.25 | 97.02 ± 9.24 |
| H | n-Propyl | 0.10 | 68.43 ± 3.24 |
| | | 0.25 | 100.19 ± 11.25 |
| H | Isopropyl | 0.10 | 34.65 ± 1.62 |
| | | 0.25 | 42.88 ± 2.93 |
| 4th Group | | | |
| Ethyl | Ethyl | 0.10 | 16.71 ± 1.84 |
| | | 0.25 | 23.65 ± 1.90 |
| Methyl | n-Propyl | 0.10 | 41.32 ± 2.55 |
| | | 0.25 | 61.60 ± 4.62 |
| n-Butyl | H | 0.10 | 56.25 ± 1.87 |
| | | 0.25 | 93.30 ± 1.65 |
| H | n-Butyl | 0.10 | 59.72 ± 3.00 |

TABLE-3-continued

| Derivative | | Concentration (mM) | Ratio of NGF increase |
|---|---|---|---|
| | | 0.25 | 88.35 ± 2.47 |
| H | sec-Butyl | 0.10 | 36.28 ± 3.49 |
| | | 0.25 | 70.11 ± 5.75 |
| H | tert-Butyl | 0.10 | 18.53 ± 1.50 |
| | | 0.25 | 18.77 ± 2.92 |
| 5th Group | | | |
| Methyl | Methyl | 0.10 | 43.62 ± 2.23 |
| | | 0.25 | 60.44 ± 3.94 |
| Methyl | n-Butyl | 0.10 | 49.83 ± 3.65 |
| | | 0.25 | 76.25 ± 6.64 |
| Methyl | tert-Butyl | 0.10 | 9.65 ± 2.42 |
| | | 0.25 | 24.19 ± 2.73 |
| n-Pentyl | H | 0.10 | 37.20 ± 1.28 |
| | | 0.25 | 51.46 ± 1.40 |
| H | n-Pentyl | 0.10 | 43.75 ± 4.71 |
| | | 0.25 | 61.03 ± 5.82 |

TABLE 4

| Derivative | Concentration (mM) | Ratio of NGF increase* 24-hr culture | 48-hr culture |
|---|---|---|---|
| 0.5% Bovine serum albumin | | 1.00 ± 0.05 | 0.99 ± 0.08 |
| 10% Fetal calf-serum | | 43.21 ± 6.20 | 48.92 ± 3.35 |
| R = Two H, | 0.10 | 77.34 ± 9.21 | 106.23 ± 7.61 |
| $R_1$ = H, $R_2$ = Methyl | 0.25 | 6.59 ± 1.34 | 2.47 ± 1.22 |
| R = Two acetyl | 0.10 | 49.82 ± 6.44 | 77.35 ± 6.52 |
| $R_1$ = H, $R_2$ = Methyl | 0.25 | 41.25 ± 7.32 | 82.37 ± 7.24 |
| R = -CO-, $R_1$ = H | 0.10 | 52.35 ± 5.29 | 73.37 ± 4.25 |
| $R_2$ = Methyl | 0.25 | 44.92 ± 4.25 | 78.32 ± 6.50 |
| R = -CO.CO-, $R_1$ = H | 0.10 | 47.24 ± 3.98 | 69.62 ± 3.25 |
| $R_2$ = Methyl | 0.25 | 50.62 ± 4.74 | 70.22 ± 5.37 |
| R = -C(CH$_3$)$_2$-, $R_1$ = H, | 0.10 | 28.62 ± 2.23 | 41.63 ± 2.21 |
| $R_2$ = Methyl | 0.25 | 33.71 ± 2.09 | 55.25 ± 4.42 |

Note: *Fold increase over reference of 24-hr culture.

Acute toxicity

Acute toxicity test in mice was carried out as a preliminary experiment to evaluate the effect in vivo of the derivative which had exhibited activity in the experimental system in vitro. Results are illustrated in Table 5.

According to the results, the acute toxicity reduces with the increase in carbon numbers of alkyl groups on the catechol ring, regardless of administration method. The tendency is particularly. remarkable in intravenous administration. When intravenous or intraperitoneal injection was performed in an amount exceeding 25% of $LD_{50}$, the derivative having lower alkyl groups on the ring was observed to cause transient convulsion in some experimental bodies. Esterified or etherified catechol derivative has been found to remarkably increase the value of $LD_{50}$ as compared with the catechol derivative having free hydroxyl groups, and also much improve the acute phase toxicity symptoms such as convulsion.

Therefore the derivative of this invention, for example, the derivative A (R=Two H, $R_1$=H, and $R_2$=n-propyl, e.g. 4-n-propylcatechol) is converted to an optional type of preparation by means of known preparing method.

The dose for adult by injection or oral route is preferably not more than 75 mg in intravenous injection, not more than 100 mg in non-intravascular administration and not more than 750 mg in oral administration. The esterified derivative may increase the dosage and the dose is respectively not more than 125 mg, not more than 375–625 mg, and not more than 1250–1500 mg.

Method of experiment

The catechol derivative having normal type saturated lower alkyl groups on the ring was administered by intravenous injection (i.v.), intraperitoneal injection (i.p.) or oral route (p.o.) to male ddy mice of 4-week old. The $LD_{50}$ values (mg/kg) were measured by an ordinary method. Results are illustrated in Table 5.

TABLE 5

| Derivative (A) | $LD_{50}$ (mg/kg) | | |
|---|---|---|---|
| | i.v. | i.p. | p.o. |
| R = Two H, $R_1$ = H | | | |
| $R_2$ | | | |
| Methyl | >50 | >200 | >500 |
| Ethyl | >75 | >300 | >1000 |
| n-Propyl | >150 | >500 | >1500 |
| n-Butyl | >150 | >500 | >1500 |
| $R_2$ = H | | | |
| $R_1$ | | | |
| Methyl | >50 | >200 | >500 |
| n-Propyl | >150 | >500 | >1500 |
| R = Two acetyl | >250 | >750 | >2500 |
| $R_1$ = H, $R_2$ = n-Propyl | | | |
| R = —CO—, $R_1$ = H | >250 | >1000 | >2500 |
| $R_2$ = n-Propyl | | | |
| R = —CO.CO—, $R_1$ = H | >250 | >1250 | >3000 |
| $R_2$ = n-Propyl | | | |
| R = —C(CH$_3$)$_2$—, $R_1$ = H | >500 | >1500 | >3500 |
| $R_2$ = n-Propyl | | | |

Activation effect on the NGF production in the central nervous system of normal rats by intraperitoneal injection The derivative having the activity for promoting the production and secretion in vitro of NGF was intended to prove the activity for accelerating the production and secretion in vivo in the central nervous system. The derivative (A), e.g. R=Two H, $R_1$=H and $R_2$=n-propyl (hereinafter referred to as 4-n-propylcatechol), was administered to normal rats by intraperitoneal injection, and the effect was examined.

4-n-Propylcatechol was administered by intraperitoneal injection 4 times every other day in a dosage of 5 mg/kg. The rats were killed two days after the final administration. The NGF content of each parts in brain was measured. The content was compared with those of control group which was administered saline alone. The results are illustrated in Table 6. A marked activation of NGF production was observed in frontal cortex, hippocampus and olfactory bulb. Significant increase in NGF level was also observed in the original region of cholinergic tracts projecting into the regions mentioned above.

A variety of the derivative was administered three times every other day. The content of NGF in the forebrain after 48 hours and 7 days from the final administration was measured and illustrated in Table 7.

The effect of alkyl groups ($R_1$ and $R_2$) on the ring was compared in a series of the derivative (A) having free hydroxyl groups (R=two H). The derivative having alkyl groups of about three carbon atoms has been found to maintain a stable level of NGF for a long period. Furthermore, the derivative having esterified hydroxyl groups has also been found to exert the same level of activity as that having free hydroxyl groups.

As a summary of above mentioned results, the derivative which activated the NGF production and secretion in vitro of the astroglial cells has been proved by the experiments in vivo to be capable of activating the NGF producing ability in the specific parts of central nervous system by the peripheral administration. A frequent administration in high dose, however, is required for exhibiting the efficacy to living bodies. Thus in consideration of the test results on acute toxicity, the derivative having normal type lower alkyl groups of about three carbon atoms in the 3 and/or 4 positions is assumed to be preferable and the esterified catechol derivative is presumed to be more preferable.

Method of experiment

Wistar male rats (9-10-week old, 200-250 g of weight) were intraperitoneally injected with the test derivative in a volume of 0.5 ml as a saline solution, emulsion or suspension. Dose and administration times were the same as above. The rats were killed by a hard spinal blow two days after the final administration. Each parts of brain were dissected and subjected to the following treatment under ice cooling.

Each parts of brain were weighed and homogenized for 30 strokes by a Dounce type homogenizer in a homogenization buffer (0.1 M Tris-HCl, containing 2% bovine serum albumin fraction V, 2% gelatin, 1.0 M NaCl, 0.02% $NaN_3$, 2 mM EDTA and 2.6 kiu/ml of aprotinin, pH 7.6) at a concentration of 10% (W/V) (only septum 5% (W/V)). Each homogenate was centrifuged at 100,000 xg for 10 minutes, and 50 μl of supernatant was added with the same amount of a dilution buffer (0.1 M Tris-HCl containing 2% bovine serum albumin fraction V, 0.05% $NaN_3$ and 20 mM $CaCl_2$, pH 7.6). Determination was conducted in accordance with a method of S. Furukawa et al. by using a high sensitivity ELISA system on 8-NGF which was described in J. Neurochem., 40, 734-744 (1983). Lower limit of determination is 0.25 pg/ml. Data are indicated as a mean value ±SE on the NGF content of tissue (pg/mg wet tissue) of five rats.

TABLE 6

| Brain tissue | NGF content (pg/mg wet tissue) | |
|---|---|---|
| | Saline | 4-n-Propylcatechol |
| Frontal cortex | 0.87 ± 0.11 | 2.14 ± 0.49* |
| Hippocampus | 2.21 ± 0.32 | 3.92 ± 0.63* |
| Olfactory bulb | 0.92 ± 0.08 | 1.70 ± 0.24** |
| Septum | 0.74 ± 0.06 | 1.39 ± 0.14** |
| Striatum | 0.22 ± 0.02 | 0.24 ± 0.04 |
| NBM*** | 0.71 ± 0.08 | 1.69 ± 0.17** |
| Cerebellum | 0.30 ± 0.09 | 0.33 ± 0.16 |

Note: Significantly different from saline administration (*$P < 0.05$, **$P < 0.01$)
***Nucleus basalis magnecellularis

TABLE 7

| Derivative (A) | NGF content (pg/mg wet tissue of frontal cortex) | |
|---|---|---|
| | After 48 hr. | After 7 days |
| Control | 0.92 ± 0.12 | 0.87 ± 0.09 |
| R = Two H, $R_1$ = H $R_2$ = Methyl | 2.26 ± 0.24** | 1.64 ± 0.46 |
| Ethyl | 1.96 ± 0.42* | 1.73 ± 0.39* |
| n-Propyl | 1.97 ± 0.41* | 2.28 ± 0.29** |
| n-Butyl | 1.88 ± 0.46* | 2.25 ± 0.33** |
| R = Two H, $R_2$ = H $R_1$ = n-Propyl | 2.03 ± 0.37** | 2.00 ± 0.43* |
| R = Two Acetyl $R_1$ = H, $R_2$ = n-Propyl | 1.71 ± 0.28** | 2.16 ± 0.46* |
| R = —CO— $R_1$ = H, $R_2$ = n-Propyl | 1.66 ± 0.23** | 2.23 ± 0.39** |

TABLE 7-continued

| Derivative (A) | NGF content (pg/mg wet tissue of frontal cortex) | |
|---|---|---|
| | After 48 hr. | After 7 days |
| R = —CO.CO— $R_1$ = H, $R_2$ = n-Propyl | 1.54 ± 0.20** | 2.02 ± 0.47* |
| R = —C(CH_3)_2— $R_1$ = H, $R_2$ = n-Propyl | 1.15 ± 0.18 | 1.51 ± 0.49 |

Note: Significantly different from saline administration (*$P < 0.05$, **$P < 0.01$)

Effects on the retention of passive avoidance learning

Effects of the derivative on the behavioral parameters of rats injected with kainic acid at basal forebrain were characterized with regard to both prevention against deficits in retention of passive avoidance learning and promotion of recovery from damaged state by repeated learning.

Table 8 illustrates the results examined on the prevention of retention disorder by 4-n-propylcatechol and its derivative having modified hydroxyl groups.

Kainic acid injected rats were markedly damaged in the retention of learning and memory. On the other hand, both derivatives which had effectively activated NGF production and secretion in vitro and in vivo exerted significant preventive effect against the regression.

Table 9 illustrates the results examined on the effect for the promotion of recovery from the retention deficits by repeated learning.

Deficits in learning and memory of kainic acid injected rats could be recovered by additional and repeated acquisition trials at every retention test. Both derivatives also accelerated this process significantly.

Methoth of experiment

Male Sprague-Dawley rats (9-10 weeks of age, 200-250 g of weight) were anesthetized with Nembutal (50 mg/kg, i.p.) and placed in a stereotaxic apparatus. Bilateral lesions of the ventral globus pallidus were made by direct stereotaxic application (0.7 mm posterior to bregma, 2.7 mm lateral to the midline, and 7.0 mm ventral to the brain surface) of 0.25 μg of kainic acid in 1 μl of PBS (pH 7.4) to prepare disordered models. Controls were sham-operated rats injected with PBS in place of kainic acid solution.

Passive avoidance procedures were performed by using a two chambered step-through passive avoidance apparatus with a guillotine door. A 3 mA scrambled shock was delivered to the dark floor grids for 3 seconds as a punishment. Habituation trial was conducted prior to the acquisition trial. Each rats were placed in the illuminated chamber and the guillotine door was raised after 10 seconds. As soon as the rats entered into the dark chamber, the door was lowered. The rats were removed after 10 seconds and returned to their home cages. Rats which did not enter into the dark chamber were omitted. The acquisition trial was performed similarly to the habituation trial. In the former case, a rat was placed in the illuminated room and the door was opened after 10 seconds. The door was shut immediately after the rat entered into the dark room, a scrambled foot shock was applied, and then the animal was removed. The latency to enter the dark chamber after opening the door was recorded for 300 seconds in the retention of passive avoidance. The latency exceeding 300 seconds was calculated as 300 seconds.

The preventive effects on deficits in retention were estimated by using 60 rats. Thirty rats were injected with kainic acid and other 30 rats were sham-operated with PBS.

Each groups of animals were equally divided into three groups which were received intraperitoneally 5 mg/kg of the derivative (A) (R=2H, $R_1$=H, $R_2$=n-propyl, that is, 4-n-propylcatechol), derivative A (R=—CO—, $R_1$=H, $R_2$=n-propyl) and saline respectively as a saline solution on one, four and seven days after the operation.

Table 8 illustrates the results obtained by conducting the acquisition trial 10 days after the operation and the retention test after 24 hours.

The promoting effects on the recovery by repeated training from the damaged state of retention were acessed by using 30 rats injected with kainic acid. Rats were subjected to the acquisition trial 10 days after the operation. The rats were equally divided into 3 groups after 24 hours and injected intrapenitroneally with 5 mg/kg of 4-n-propylcatechol and the derivative (A) (R=—CO—, R=H, $R_2$=n-propyl) respectively as a saline solution. The remaining 10 rats were intraperitoneally injected with saline alone. The first retention trial was carried out two days after the injection. Rats which entered into the dark chamber within 30 seconds were punished by the scrambled foot shock as a training. On the next day, all animals were administered again the same amount of test derivative or saline. These animals were subjected to the second retention trial two days after the second injection.

Retention trials, punishments and additional administrations were repeated as mentioned above four times in all. Data were compared among each retention trial and the results are illustrated in Table 9.

TABLE 8

| Animals | Mean latency (sec) | Animals with more than 150 sec of latency (in 10 animals) |
| --- | --- | --- |
| Scham-operated rats injected with | | |
| Saline | 280 ± 5 | 10 |
| 4-n-Propylcatechol | 286 ± 9 | 10 |
| Derivative (A) (R = —CO—, $R_1$ = 1, $R_2$ = n-propyl) | 291 ± 7 | 10 |
| Operated rats with kainic acid injected with | | |
| Saline | 27 ± 11 | 0 |
| 4-n-propylcatechol | 114 ± 44* | 3 |
| Derivative (A) (R = —CO—, $R_1$ = H, $R_2$ = n-propyl) | 152 ± 29* | 4 |

Note: Significantly different from controls in the same operation (*P < 0.01)

TABLE 9

| Retention trial | Saline (control) | Mean latency Rats injected with Derivative (A) (R = 2H, $R_1$ = H, $R_2$ = n-propyl) | Deivative (A) ($R_1$ = —CO —, $R_1$ = H, $R_2$ = n-propyl) |
| --- | --- | --- | --- |
| 1st | 24 ± 12 | 47 ± 16 | 46 ± 13 |
| 2nd | 98 ± 19 | 147 ± 29 | 167 ± 31* |
| 3rd | 149 ± 30 | 201 ± 23 | 236 ± 28* |
| 4th | 201 ± 23 | 272 ± 14** | 284 ± 15** |

Note: Significantly different from controls in the same retention trial (*P < 0.05, **P < 0.01)

EXAMPLES

The present invention will hereinafter be illustrated in detail with respect to the following examples without restricting the scope of this invention.

EXAMPLE 1

Preparation of 3,4-diisobutyryloxytoluene

A mixture of 1.0 g (8 mM) of homocatechol and 2.8 g (18 mM) of isobutyric anhydride was added with a drop of concentrated sulfuric acid at the room temperature with a slow stirring. An exothermic reaction was immediately initiated. After completing the exothermic reaction, the reaction mixture was poured into ice water. The separated oil was extracted with ether and dried with anhydrous magnesium sulfate. Then the solution was filtered, concentrated and distilled under vacuum to obtain 2.0 g (7.6 mM) of 3,4-diisobutyryloxytoluene as a colorless transparent liquid having a boiling point of 67°–68° C./4 mmHg.

IR Spectrum $\nu_{max}^{neat}$cm$^{-1}$: 2980, 2940, 2880, 1765, 1615, 1600, 1510, 1470, 1390, 1350, 1300, 1260, 1235, 1205, 1185, 1115, 1045, 950, 910, 805, 790, 750

NMR Spectrum (CDCl$_3$) δ:1.29 (12H, d), 2.26–2.34 (3H), 2.76 (2H, sep), 6.76–6.96 (3H)

Elementary Analysis [C$_5$H$_{20}$O$_4$]:

| | C | H |
| --- | --- | --- |
| Calculated (%) | 68.16 | 7.63 |
| Found (%) | 67.99 | 7.66 |

EXAMPLE 2

Preparation of 4-ethyl-1,2-diacetoxybenzene (1) Preparation of 4-ethylveratrole

In an atmospheric pressure hydrogenation equipment 10.0 g (60.9 mM) of 3,4-dimethoxystyrene, 0.5 g of palladium charcoal and 200 ml of methanol were charged and introduced with hydrogen. The reaction was continued until the absorption of hydrogen was terminated. Palladium charcoal was filtered off from the reaction mixture. Methanol was distilled off from the filtrate. The residue was distilled under vacuum to obtain 10.0 g (60.2 mM) of 4-ethylveratrole as a colorless transparent liquid having a boiling point of 84°–85° C./2 mmHg IR Spectrum $\nu_{max}^{neat}$cm$^{-1}$: 2960, 2930, 2880, 2840, 1600, 1590, 1510, 1460, 1415, 1265, 1230, 1155, 1140, 1025, 900, 845, 800, 760

NMR Spectrum (CDCl$_3$) δ:1.18 (3H, t), 2.52 (2H, q), 3.69–3.72 (6H), 6.65 (3H)

Elementary Analysis [C$_{10}$H$_{14}$O$_2$]:

| | C | H |
| --- | --- | --- |
| Calculated (%) | 72.26 | 8.49 |
| Found (%) | 71.99 | 8.54 |

(2) Preparation of 4-ethylcatechol

A mixture of 10.0 g (60.2 mM) of 4-ethylveratrole, 38.4 g (639 mM) of acetic acid and 115.0 g (668 mM) of 47% hydrobromic acid was heated under reflux for 4 hours with stirring. After cooling to the room temperature, 100 ml of water was added and the resultant mixture was extracted three times with each 110 ml of ether. The ether extract was successively washed with 110 ml of water, 150 g of 5% aqueous sodium thiosulfate solution and further twice with each 110 ml of water. The resulting ether solution was dried with anhydrous sodium sulfate, filtered, concentrated and distilled under vacuum to obtain 7.4 g (53.6 mM) of 4-ethylcatechol as a light yellow liquid having a boiling point of 111°-112° C./4 mmHg.

IR Spectrum $v_{max}^{neat}cm^{-1}$: 3380, 3040, 2960, 2925, 2880, 1605, 1525, 1445, 1350, 1280, 1190, 1150, 1110, 1060, 980, 920

NMR Spectrum (CDCl$_3$): δ:1.04 (3H, t), 2.36 (2H, q), 6.00-7.25 (5H)

Elementary Analysis [C$_8$H$_{10}$O$_2$]:

|  | C | H |
|---|---|---|
| Calculated (%) | 69.54 | 7.30 |
| Found (%) | 69.25 | 7.46 |

(3) Preparation of 4-ethyl-1,4-diacetoxybenzene

A mixture of 4.6 g (33 mM) of 4-ethylcatechol and 7.5 g (73 mM) of acetic anhydride was added with a drop of concentrated sulfuric acid at the room temperature. An exothermic reaction was immediately initiated. After cooling to the room temperature, the reaction mixture was poured into ice water. The separated oil was extracted with ether. The extracted solution was dried with anhydrous sodium sulfate, filtered, concentrated and distilled under vacuum to obtain 7.1 g (32 mM) of 4-ethyl-1,2-diacetoxybenzene as a colorless transparent liquid having a boiling point of 116°-117° C./3 mmHg.

IR Spectrum $v_{max}^{neat}cm^{-1}$: 2970, 2940, 2880, 1770, 1610, 1590, 1505, 1425, 1370, 1260, 1210, 1180, 1145, 1115, 1060, 1045, 1010, 935, 900, 885, 855, 830 795

NMR Spectrum (CDCl$_3$) δ:1.20 (3H, t), 2.20 (6H, s), 2.60 (2H, q), 7.20-7.55 (3H)

Elementary Analysis [C$_{12}$H$_{14}$O$_4$]:

|  | C | H |
|---|---|---|
| Calculated (%) | 64.85 | 6.35 |
| Found (%) | 64.61 | 6.41 |

EXAMPLE 3

Preparation of 1,2-diacetoxy-4-propylbenzene (1) Preparation of 4-propylveratrole An atmospheric pressure hydrogenation equipment was charged with 17.8 g (0.10 M) of 1,2-dimethoxy-4-propenylbenzene, 0.9 g of palladium charcoal and 350 ml of methanol and introduced with hydrogen. The reaction was continued until the absorption of hydrogen was terminated. Palladium charcoal was filtered off from the reaction mixture. The filtrate was distilled off methanol and vacuum distilled to obtain 17.5 g (0.097 M) of 4-propylveratrole as colorless transparent liquid having a boiling point of 106°-108° C./4 mmHg.

IR Spectrum $v_{max}^{neat}cm^{-1}$: 2980, 2950, 2930, 2870, 2840, 1600, 1585, 1510, 1460, 1415, 1375, 1340, 1320, 1260, 1230, 1185, 1155, 1140, 1080, 1025, 930, 860, 840, 800, 755

NMR Spectrum (CDCl$_3$) δ:0.94 (3H, t), 1.60 (2H, sex), 2.50 (2H, t), 3.76-3.79 (6H), 6.62-6.64 (3H)

Elementary Analysis [C$_{11}$H$_{16}$O$_2$]:

|  | C | H |
|---|---|---|
| Calculated (%) | 73.30 | 8.95 |
| Found (%) | 73.08 | 8.97 |

(2) Preparation of 4-propylcatechol

A mixture of 15.0 g (83 mM) of 4-propylveratrole, 53.0 g (882 mM) of acetic acid and 159.4 g (926 mM) of 47% hydrobromic acid was heated under reflux for 2 hours with stirring. After cooling to the room temperature, the reaction mixture was added with 140 ml of water and extracted three times with each 150 ml of ether. The extracted ether solution was successively washed with 150 ml of water, 150 g of 5% aqueous sodium thiosulfate solution and then twice with each 150 ml of water. The resulting solution was dried with anhydrous sodium sulfate, distilled off ether and vacuum distilled to obtain 10.5 g (69 mM) of 4-propylcatechol as a light yellow liquid having a boiling point of 119° C/3 mmHg.

IR Spectrum $v_{max}^{neat}cm^{-1}$: 3450, 3325, 3030, 2915, 2850, 1620, 1600, 1515, 1460, 1340, 1290, 1275, 1255, 1225, 1180, 1145, 1115, 955, 860, 810, 790, 740, 720, NMR Spectrum (CDCl$_3$) δ:0.88 (3H, t), 1.52 (2H, sex), 2.38 (2H, t), 5.2-6.4 (2H, s, broad), 6.51-6.78 (3H)

Elementary Analysis [C$_9$H$_{12}$O$_2$]:

|  | C | H |
|---|---|---|
| Calculated (%) | 71.03 | 7.95 |
| Found (%) | 71.04 | 7.83 |

(3) Preparation of 1,2-diacetoxy-4-propylbenzene

A mixture of 2.7 g (18 mM) of 4-propylcatechol and 4.1 g (40 mM) of acetic anhydride was added with a drop of concentrated sulfuric acid. An exothermic reaction was immediately initiated. After cooling to the room temperature the reaction was poured into ice water. The separated oil was extracted with ether, dried with anhydrous sodium sulfate, and distilled off ether. The residue was vacuum distilled to obtain 4.2 g (17 mM) of 1,2-diacetoxy-4-propylbenzene as colorless transparent liquid having a boiling point of 111°-119° C./ 4 mmHg.

IR Spectrum $v_{max}^{neat}cm^{-1}$: 2960, 2930, 2880, 1770, 1610, 1595, 1505, 1465, 1425, 1370, 1260, 1220, 1205, 1180, 1145, 1115, 1040, 1010, 960, 900, 825, 790

NMR Spectrum (CDCl$_3$) δ:0.90 (3H, t), 1.60 (2H, sex), 2.95 (6H, s), 2.54 (2H, t), 6.92-7.02 (3H Elementary Analysis [C$_{13}$H$_{16}$O$_4$]:

|  | C | H |
|---|---|---|
| Calculated (%) | 66.09 | 6.82 |
| Found (%) | 65.81 | 6.81 |

EXAMPLE 4

Preparation of 1,2-acetoxy-4-n-butylbenzene (1) Preparation of 4-n-butyrylveratrole A mixture of 41.45 g (0.30 M) of veratrole, 52.21 g (0.33 M) of n-butyric anhydride and 1.52 g (12 mg atom)

of iodine was heated under reflux for 7 hours, with stirring. After cooling to the room temperature, the reaction mixture was poured into 150 ml of water and extracted three times with each 150 ml of ether. The extracted ether solution was successively washed with 150 g of 12% aqueous sodium carbonate solution, 150 g of 2% aqueous sodium hydrogen sulfite solution and then twice with each 150 ml of water. The resulting solution was dried with anhydrous sodium sulfate and distilled off ether. The residue was recrystallized from an aqueous methanol solution to obtain 52.59 g (0.25 M) of 4-n-butyrylveratrole as light yellow crystals having a melting point of 52°-53° C.

IR Spectrum $\nu_{max}^{KBr}$cm$^{-1}$: 3060, 2910, 2830, 1650, 1580, 1500, 1460, 1445, 1405, 1395, 1300, 1250, 1230, 1190, 1180, 1140, 1010, 900, 880, 860, 795, 740.

NMR Spectrum (CDCl$_3$) δ:1.02 (3H, t), 1.78 (2H, sex), 2.91 (2H, t), 3.96 (6H, s), 6.86-6.94 (1H), 7.56-7.65 (2H)

Elementary Analysis [C$_{12}$H$_{16}$O$_3$]:

|  | C | H |
| --- | --- | --- |
| Calculated (%) | 69.21 | 7.74 |
| Found (%) | 68.97 | 8.00 |

(2) Preparation of 4-n-butylveratrole

A mixture of 68 ml of diethylene glycol and 12 g (0.18 M) of potassium hydroxide was gradually heated to 190° C. with stirring while distilling off low boiling fraction. The reaction mixture was allowed to cool to 80°-100° C. after termination of the heating and added with 12.7 g (0.061 M) of 4-n-butyrylveratrole and 7.6 g (0.152 M) of hydrazine hydrate. The reaction flask was fitted with a reflux condenser, gradually heated to the reflux temperature and the temperature was maintained for an hour with stirring. Thereafter the reaction mixture was gradually heated to 205°-210° C. while distilling off the low boiling fraction and heating was further continued under reflux for 3 hours. The reaction mixture was gradually cooled to 100°-110° C. after termination of the heating and poured into 60 ml of water. The flask was washed with 40 ml of water and the water was added to the above water layer. The pH of the resulting mixture was reduced to 5.0 by using 6N hydrochloric acid. The separated oil was extracted with ether, washed with water and dried with anhydrous sodium sulfate. The solution was distilled off ether and vacuum distilled to obtain 8.8 g (0.046 M) of 4-n-butylveratrole as colorless transparent liquid having, a boiling point of 105°-107° C./5 mmHg.

NMR Spectrum (CDCl$_3$) δ:0.92 (3H, t), 1.10-1.76 (4H, m), 2.52 (2H, t), 3.82-3.84 (6H), 6.56-6.88 (6H)

(3) Preparation of 4-n-butylcatechol

A mixture of 5.64 g (29 mM) of 4-n-butylveratrole, 18.54 g (309 mM) of acetic acid and 55.62 g (323 mM) of 47% hydrobromic acid was heated under reflux for 4 hours with stirring. The reaction mixture was cooled to the room temperature and added with 50 ml of eater. The separated oil was extracted with ether. The ether solution was successively washed with 50 ml of water, 75 g of 5% aqueous sodium thiosulfate solution, and further twice with each 50 ml of water. The resulting solution was dried with anhydrous sodium sulfate, distilled off ether, and vacuum distilled to obtain 3.89 g (23 mM) of n-butylcatechol as light yellow liquid having a boiling point of 125° C./3 mmHg.

IR Spectrum $\mu_{max}^{neat}$cm$^{-1}$: 3340, 3020, 2940, 2920, 2855, 1600, 1510, 1435, 1340, 1280, 1240, 1185, 1140, 1105, 945, 850, 800, 775, 740

IR NMR Spectrum (CDCl$_3$) δ:0.88 (3H, t), 1.40 (4H, m), 2.40 (2H, t), 6.0-7.2 (5H)

Elementary Analysis [C$_{10}$H$_{14}$O$_2$]:

|  | C | H |
| --- | --- | --- |
| Calculated (%) | 72.26 | 8.49 |
| Found (%) | 72.01 | 8.69 |

(4) Preparation of 1,2-diacetoxy-4-n-butylbenzene

A mixture of 2.0 g (12 mM) of 4-n-butylcatechol and 2.8 g (27 mM) of acetic anhydride was added with a drop of concentrated sulfuric acid. An exothermic reaction was immediately initiated. After cooling to the room temperature, the reaction mixture was poured into ice water. The separated oil was extracted with ether and dried with anhydrous sodium sulfate. The resulting solution was distilled off ether and vacuum distilled to obtain 2.8 g (11 mM) of 1,2-diacetoxy-4-n-butylbenzene as colorless transparent liquid having a boiling point of 88°-90° C./2 mmHg.

IR Spectrum $\nu_{max}^{neat}$cm$^{-1}$: 3030, 2960, 2935, 2880, 2870, 1770, 1615, 1595, 1505, 1470, 1425, 1370, 1270, 1260, 1210, 1180, 1145, 1115, 1040, 1010, 960, 900, 890, 850, 830.

NMR Spectrum (CDCl$_3$) δ:0.90 (3H, t), 1.44 (4H, m), 2.22 (6H, s), 2.60 (2H, t), 6.92-6.98 (3H)

Elementary Analysis [C$_{14}$H$_{18}$O$_4$]:

|  | C | H |
| --- | --- | --- |
| Calculated (%) | 67.18 | 7.25 |
| Found (%) | 66.90 | 7.49 |

EXAMPLE 5

Preparation of 6-methyl-1,4-benzodioxine-2,3-dione

A mixture of 12.41 g (0.10 M) of homocatechol, 20.24 g (0.20 M) of triethylamine, and 225 ml of dry ethyl ether was added dropwise under stirring over an hour with a solution of 14.10 g (0.11 M) of oxalyl chloride in 30 ml of dry ethyl ether. The reaction mixture was cooled in a water bath so as to maintain the reaction temperature at 27°-30° C., and aged for 3 hours at the same temperature after completing the addition. The resulting mixture was concentrated under reduced pressure to obtain 47.5 g of a solid mass. The solid mass was extracted three times with each 150 ml of hot benzene under nitrogen atmosphere. The benzene extract was collected and concentrated under reduced pressure. The crude product thus obtained was purified by sublimation at a both temperature of 80°-120° C. under pressure of 2-4 mmHg. The crystals obtained were 16.25 g and recrystallized from benzene under nitrogen atmosphere to yield 14.11 g (0.08 M) of 6-methyl-1,4-benzodioxine-2,3-dione as colorless crystals having a melting point of 121°-123° C.

IR Spectrum $\nu_{max}^{KBr}$cm$^{-1}$: 3100, 3075, 2975, 2950, 2880, 1815, 1780, 1615, 1515, 1465, 1430, 1395, 1360, 1330, 1315, 1280, 1265, 1220, 1185, 1160, 1135, 1120, 1050, 1015, 965, 905, 885, 820, 800, 760, 735, 720.

NMR Spectrum (CDCl$_3$) δ:2.42 (3H, s), 7.02–7.42 (3H)

Elementary Analysis [C$_9$H$_6$O$_4$]:

|  | C | H |
| --- | --- | --- |
| Calculated (%) | 60.68 | 3.39 |
| Found (%) | 60.39 | 3.27 |

EXAMPLE 6

Preparation of 6-ethyl 1,4-benzodioxine-2,3-dione

A mixture of 3.46 g (25 mM) of 4-ethylcatechol, 50 ml of dry ether was added dropwise with 3.50 g (28 mM) of oxalyl chloride over 2 hours while heating under reflux. The stirring was continued until the end of gas evolution. The reaction mixture was concentrated to dryness and recrystallized from a solvent mixture of benzene and petroleum benzine to obtain 4.79 g (21 mM) of 6-ethyl-1,4-benzodioxine-2,4-dione dihydrate as colorless crystals having a melting point of 99°–104° C.

IR Spectrum $\nu_{max}^{KBr}$cm$^{-1}$: 3340, 2965, 2930, 2875, 1775, 1740, 1605, 1525, 1510, 1435, 1355, 1320, 1300, 1280, 1265, 1225, 1180, 1110, 1060, 985, 945, 920, 885, 850, 815, 795, 750, 735, 715, 700.

NMR Spectrum (DMSO-d$_6$): δ:1.18 (3H, t), 2.54 (2H, q), 6.6–7.0 (3H), 5.5–8.0 (4H, broad).

Elementary Analysis [C$_{10}$H$_{12}$O$_6$]:

|  | C | H |
| --- | --- | --- |
| Calculated (%) | 52.63 | 5.30 |
| Found (%) | 52.35 | 5.18 |

EXAMPLE 7

Preparation of 6-n-propyl-1,4-benzodioxine-2,3-dione

A mixture of 3.81 g (25 mM) of 4-n-propylcatechol, 5.06 g (50 mM) of triethylamine and 50 ml of dry ether was cooled in an ice water bath so as to maintain the temperature at 5° C. or below. The mixture was added dropwise over 1.5 hours under stirring with a solution of 3.50 g (28 mM) of oxalyl chloride in 10 ml of dry ether. After completing the dropwise addition, the temperature of the reaction mixture was gradually raised to the room temperature and then aging was conducted for an hour. The resultant mixture was heated under reflux for 3 hours in order to complete the aging. The separated crystals of triethyl ammonium chloride was filtered. After thoroughly washing the crystals with ether, the ether solution was collected and dried with anhydrous sodium sulfate. After distilling off ether, the reaction product was recrystallized from a solvent mixture of carbontetrachloride and petroleum benzine to obtain 4.64 g (22.5 mM) of 6-n-propyl-1,4-benzodioxine-2,3-dione monohydrate as colorless crystals having a melting point of 99°–100° C.

IR Spectrum $\nu_{max}^{KBr}$cm$^{-1}$: 3330, 3050, 2955, 2925, 2825, 1780, 1770, 1605, 520, 1465, 1430, 1340, 1305, 1280, 1235, 1180, 1110, 960, 940, 890, 860, 810, 790, 750, 730, 700.

NMR Spectrum (DMSO-d$_6$) δ:0.91 (3H, t), 1.54 (2H, sex), 2.47 (2H, t), 6.4–7.0 (3H), 8.4–9.8 (2H)

Elementary Analysis [C$_{11}$H$_{12}$O$_5$]:

|  | C | H |
| --- | --- | --- |
| Calculated (%) | 58.93 | 5.39 |
| Found (%) | 58.63 | 5.56 |

EXAMPLE 8

Preparation of 6-n-butyl-1,4-benzodioxine-2,3-dione

A mixture of 4.16 g (25 mM) of 4-n-butylcatechol, 5.06 g (50 mM) of triethylamine and ml of dry ether was cooled in an ice water bath so as to maintain the temperature at 5° C. or below. The mixture was added dropwise over 2 hours under stirring with a solution of 3.50 g (28 mM) of oxalyl chloride in 10 ml of dry ether. After completing the dropwise addition, the temperature of the reaction mixture was gradually raised to the room temperature and then aging was conducted for an hour. The resultant mixture was heated under reflux for 3 hours in order to complete the aging. The separated crystals of triethyl ammonium chloride was filtered. After thoroughly washing the crystals with ether, the ether solution was collected and dried with anhydrous sodium sulfate. After distilling off ether, the reaction product was recrystallized from a solvent mixture of carbontetrachloride and petroleum benzine to obtain 5.26 g (23 mM) of 6-n-butyl-1,4-benzodioxine-2,3-dione 2/5 hydrate as colorless crystals having a melting point of 88°–93° C.

IR Spectrum $\nu$max$^{KBr}$ cm$^{-1}$: 3320, 3060, 2960, 2935, 2875, 1810, 1785, 1605, 1510, 1470, 1460, 1435, 1305, 1260, 1220, 1180, 1155, 1135, 1120, 1005, 970, 905, 880, 820, 805, 735, 710.

NMR Spectrum (DMSO-d$_6$) δ:0.94 (3H, t, 1.14–1.72 (4H, m), 2.61 (2H, t), 6.54–7.16 (3H), 6.2–7.2 (0.8H)

Elementary Analysis [C$_{12}$H$_{12.8}$O$_{4.4}$]:

|  | C | H |
| --- | --- | --- |
| Calculated (%) | 63.37 | 5.67 |
| Found (%) | 63.28 | 5.95 |

EXAMPLE 9

Preparation of 6-iso-butyl-1,4-benzodioxine-2,3-dione (1) Preparation of 4-iso-butyrylveratrole A mixture of 69.09 g (500 mM) of veratrole, 87.01 g (550 mM) of isobutyric anhydride and 2.50 g (20 mM) of iodine was heated with stirring under reflux for 34 hours. After cooling to the room temperature, the reaction mixture was poured into 250 ml of water and extracted three times with each 200 ml of ether. The extracted solution was successively washed with 250 g of 12% aqueous sodium carbonate solution, 2% aqueous sodium hydrogen sulfite solution and further twice with each 250 ml of water. The resulting solution was dried with anhydrous sodium sulfate, distilled off ether and vacuum distilled to obtain 87.21 g (419 mM) of 4-iso-butyrylveratrole as yellow liquid having a boiling point of 125°–128° C./2 mmHg.

IR Spectrum $\nu_{max}^{neat}$ cm$^{-1}$: 3070, 2960, 2930, 2870, 2840, 1670, 1590, 1580, 1510, 1460, 1415, 1380, 1345, 1265, 1260, 1200, 1175, 1140, 1100, 1020, 890, 875, 830, 805, 760, 750.

NMR Spectrum (CDCl$_3$) δ:1.21 (6H, d), 3.55 (2H, sept), 3.96 (6H, s), 6.88–6.96 (1H), 7.54–7.66 (2H)

Elementary Analysis [C$_{12}$H$_{16}$O$_3$]:

|  | C | H |
|---|---|---|
| Calculated (%) | 69.21 | 7.74 |
| Found (%) | 68.93 | 7.01 |

(2) Preparation of 4-iso-butylveratrole

A mixture of 400 ml of diethylene glycol and 72.59 g (1,100 mM) of potassium hydroxide was gradually heated to 190° C. while distilling off low boiling fraction. The reaction mixture was allowed to cool to 80°–100° C. after termination of the heating and added with 70.75 g (340 mM) of 4-isobutyrylveratrole and 42.52 g (849 mM) of hydrazine hydrate. The reaction flask was fitted with a reflux condenser, gradually heated to the reflux temperature and the temperature was maintained for 2 hours with stirring. Thereafter the reaction mixture was gradually heated to 205°–210° C. while distilling off the low boiling fraction, and heating was further continued for 3 hours under reflux.

The reaction mixture was gradually cooled to 100°–110° C. after termination of the heating and poured into 300 ml of water. The flask was washed with 200 ml of water and the water was added to the above water layer. The pH of the resultant mixture was reduced to 2.0 by using 6N hydrochloric acid. The separated oil was extracted with ether, washed with water and dried with anhydrous sodium sulfate. The solution was distilled off ether and vacuum distilled to obtain 55.50 g (286 mM) of 4-isobutylveratrole as colorless liquid having a boiling point of 115°–118° C./2 mmHg.

NMR Spectrum (CDCl$_3$): δ:0.89 (6H, d), 1.83 (1H, nona), 2.39 (2H, d), 3.76–3.78 (6H), 6.49–6.82 (3H)

(3) Preparation of 4-iso-butylcatechol

A mixture of 50.83 g (262 mM) of 4-isobutylveratrole, 167.82 g (2.795 mM) of acetic acid and 502.18 g (2.917 mM) of 47% hydrobromic acid was heated under reflux for 19 hours with stirring. The reaction mixture was cooled to the room temperature and added with 400 ml of water. The separated oil was extracted with ether. The ether solution was successively washed with 400 ml of water, 660 g of aqueous sodium thiosulfate solution, and further twice with each 400 ml of water. The resulting solution was dried with anhydrous sodium sulfate, distilled off ether, and vacuum distilled to obtain 35.68 g (215 mM) of 4-iso-butylcatechol as yellow viscous liquid having a boiling point of 117°–120° C./2 mmHg.

IR Spectrum $v_{max}^{neat}$ cm$^-$: 3300 (broad), 3050, 2950, 2910, 2870, 1605, 1525, 1465, 1440, 1400, 1380, 1365, 1350, 1295, 1280, 1250, 1205, 1195, 1150, 1110, 1085, 970, 940, 920, 875, 865, 825, 800, 785, 750.

NMR Spectrum (CDCl$_3$) δ:0.85 (6H, d), 1.72 (1H, nona), 2.31 (2H, d), 5.7–6.3 (2H, broad), 6.43–6.74 (3H)

Elementary Analysis [C$_{10}$H$_{14}$O$_2$]:

|  | C | H |
|---|---|---|
| Calculated (%) | 72.26 | 8.49 |
| Found (%) | 71.98 | 8.77 |

(4) Preparation of 6-iso-butyl-1,4-benzodioxine-2,3-dione

The same procedures as described in Example 8 were carried out by using 4.16 g (25 mM) of 4-isobutylcatechol, 5.06 g (50 mM) of triethylamine and 3.50 g (28 mM) of oxalyl chloride. 6-iso-Butyl-1,4-benzodioxine-2,3-dione 2/5 hydrate was obtained in the yield of 5.11 g (22.5 mM) as colorless crystals having a melting point of 92°–97° C.

IR Spectrum $v_{max}^{KBr}$ cm$^{-1}$: 3350, 3040, 2940, 2920, 2865, 1805, 1790, 1780, 1630, 1510, 1460, 1450, 1430, 1380, 1365, 1300, 1260, 1250, 1215, 1175, 1150, 1130, 1060, 1040, 1020, 1005, 970, 935, 900, 885, 820, 790.

NMR Spectrum (DMSO-d$_6$) δ:0.91 (6H, t), 1.86 (1H, nona), 2.49 (2H, d), 4.4–5.4 (0.8 H), 6.50–7.16 (3H).

Elementary Analysis [C$_{12}$H$_{12.8}$O$_{4.4}$]:

|  | C | H |
|---|---|---|
| Calculated (%) | 63.37 | 5.67 |
| Found (%) | 63.61 | 5.76 |

EXAMPLE 10

Preparation of 5,2,2-trimethyl-1,3-benzodioxol

A mixture of 6.21 g (50 mM) of homocatechol (commercially available special grade reagent), 15 ml of acetone, 30 mg of p-toluenesulfonic acid monohydrate and 15 ml of benzene was heated under reflux for 48 hours with stirring. During the reaction, a three-component azeotropic mixture composed of acetone, benzene and water as a by-product was passed through a molecular sieve packed column to remove only the by-product water. Acetone and benzene were returned to the reaction system.

After completing the reaction, the reaction mixture was distilled in vacuum to obtain 7.88 g (48 mM) of 5,2,2-trimethyl-1,3-benzodioxol as light brown liquid having a boiling point of 79°–80° C./9 mmHg.

IR Spectrum $v_{max}^{neat}$ cm$^{-1}$: 2990, 2920, 2870, 1500, 1440, 1380, 1350, 1255, 1230, 1155, 1120, 1070, 1040, 980, 930, 880, 840, 825, 795, 745.

NMR Spectrum [C$_{10}$H$_{12}$O$_2$]:

|  | C | H |
|---|---|---|
| Calculated, (%) | 73.15 | 7.37 |
| Found (%) | 72.87 | 7.13 |

EXAMPLE 11

Preparation of 5-ethyl-2,2-dimethyl-1,3-benzodioxol

A mixture of 6.91 g (50 mM) of 4-ethylcatechol, 4.43 g (105 mM) of 90% sodium hydroxide and 200 ml of 1-butanol was heated to 70° C. with stirring and added dropwise with 6.55 g (55 mg) of 2,2-dichloropropane over 2 hours. After aging for an hour at this temperature, the reaction mixture was further heated under reflux for 3 hours with stirring. Sodium chloride formed was filtered and washed. 1-Butanol was distilled off under reduced pressure. The residue was vacuum distilled to obtain 5.08 g (29 mM) of 5-ethyl-2,2-dimethyl-1,3-benzodioxol as light brown liquid having a boiling point of 103°–105° C./12 mmHg.

In addition, 4-ethylcatechol employed as the starting material was prepared by the following process. 3,4-Dimethoxystyrene was hydrogenated in methanol in the presence of Pd/c catalyst. The methyl groups of resulting 4-ethylveratrole were removed by acetic acid and hydrogen bromide to obtain 4-ethylcatechol.

IR Spectrum $v_{max}^{neat}$ cm$^{-1}$: 3030, 2985, 2960, 2935, 2880, 1500, 1450, 1385, 1380, 1365, 1320, 1275, 1260, 1230, 1160, 1120, 1060, 980, 920, 835, 805, 785.

NMR Spectrum (CDCl$_3$) δ:1.20 (3H, t), 1.69 (6H, s), 2.58 (2H, q).

Elementary Analysis [C$_{11}$H$_{14}$O$_2$]:

|  | C | H |
| --- | --- | --- |
| Calculated (%) | 74.13 | 7.92 |
| Found (%) | 73.89 | 7.86 |

EXAMPLE 12

Preparation of 5-n-propyl-2,2-dimethyl-1,3-benzodioxol

The same procedures as described in Example 10 were carried out by using a mixture of 7.61 g (50 mM) of 4-n-propylcatechol, 15 ml of acetone, 30 mg of p-toluenesulfonic acid monohydrate and 15 ml of benzene. 5-n-Propyl-2,2-dimethyl-1,3-benzodioxol was obtained in the yield of 9.13 g (47 mM) as colorless transparent liquid having a boiling point of 82°-87° C./3 mmHg.

In addition, 4-n-propylcatechol employed as the starting material was prepared by the following process. 1,2-Dimethoxy-4-n-propenylbenzene was hydrogenated in the presence of methanol and methyl groups of resulting 4-n-propylveratrole were removed by acetic acid and hydrogen bromide to give 4-n-propylcatechol.

IR Spectrum $v_{max}^{neat}$ cm$^{-1}$: 3060, 3015, 2970, 2940, 2920, 2860, 1600, 1490, 1440, 1370, 1330, 1260, 1245, 1220, 1210, 1145, 1115, 1070, 975, 925, 860, 825, 795, 780, 755.

NMR Spectrum (CDCl$_3$) δ:0.92 (3H, t), 1.65 (6H, s), 1.57 (2H, sex), 2.48 (2H, t), 6.38–6.72 (3H).

Elementary Analysis [C$_{12}$H$_{16}$O$_2$]:

|  | C | H |
| --- | --- | --- |
| Calculated (%) | 74.97 | 8.39 |
| Found (%) | 74.81 | 8.43 |

EXAMPLE 13

Preparation of 5-n-butyl-2,2-dimethyl-1,3-benzodioxol

The same procedures as described in Example were carried out by using 4.16 g (25 mM) of.4-n-butylcatechol, 15 ml of acetone, 30 mg of p-toluenesulfonic acid monohydrate and 7 ml of benzene. 5-n-Butyl-2,2-dimethyl 1,3 benzodioxol was obtained in the yield of 4.74 g (23 mM) as colorless transparent liquid having a boiling point of 74°-75° C./1 mmHg.

In addition, the raw material 4-n-butylcatechol was prepared by the following process.

Veratrole was reacted with n-butyric anhydride in the presence of iodine. Resulting 4-n-butyrylveratrol was reduced with hydrazine hydrate and potassium hydroxide in diethyleneglycol. The methyl groups of 4-n-butylveratrole thus obtained were removed by acetic acid and hydrogen bromide to obtain 4-n-butylcatechol.

IR Spectrum $v_{max}^{neat}$ cm$^{-1}$: 3060, 3010, 2975, 2940, 2920, 2860, 2845, 1600, 1495, 1440, 1380, 1370, 1265, 1250, 1225, 1210, 1150, 1115, 1075, 975, 935, 830, 795, 780, 760, 745.

NMR Spectrum (CDCl$_3$) δ:0.92 (3H, t), 1.08–1.80 (4H, m), 1.64 (6H, s), 2.50 (2H, t), 6.4–6.68 (3H)

Elementary Analysis [C$_{13}$H$_{18}$O$_2$]:

|  | C | H |
| --- | --- | --- |
| Calculated (%) | 75.69 | 8.80 |
| Found (%) | 75.42 | 9.05 |

EXAMPLE 14

Preparation of 5-isobutyl-2,2-dimethyl-1,3-benzodioxol

The same procedures as described in Example 10 were carried out by using 4.16 g (25 mM) of 4-isobutylcatechol, 15 ml of acetone, 30 mg of p-toluenesulfonic acid monohydrate and 15 ml of toluene. 5-Isobutyl-2,2-dimethyl-1,3-benzodioxol was obtained in the yield of 4.69 g (23 mM) as colorless transparent liquid having a boiling point of 79°-83° C./2 mmHg.

In addition, the starting material 4-isobutylcatechol was prepared by using isobutyric anhydride in place of n-butyric anhydride in the process of preparing the starting material in Example 4.

IR Spectrum $v_{max}^{neat}$ cm$^{-1}$: 3060, 3025, 2980, 2950, 2920, 2870, 2845, 1605, 1495, 1465, 1450, 1440, 1380, 1375, 1365, 1330, 1285, 1270, 1255, 1235, 1220, 1165, 1155, 1120, 1085, 1070, 980, 930, 920, 875, 860, 840, 795, 765.

NMR Spectrum (CDCl$_3$) δ:0.85 (6H, d), 1.4–2.0 (1H, m), 1.65 (6H, s), 2.37 (2H, d), 6.3–6.7 (3H).

Elementary Analysis [C$_{13}$H$_{18}$O$_2$]:

|  | C | H |
| --- | --- | --- |
| Calculated (%) | 75.69 | 8.80 |
| Found (%) | 75.46 | 9.04 |

EXAMPLE 15

Preparation of 4-methyl-o-phenylenecarbonate

Under nitrogen atmosphere, 12.41 g of homocatechol was dropwise added with 25 ml of an aqueous solution containing 8.8 g of sodium hydroxide under cooling. The mixture was cooled in an ice bath, and dropwise added with 75 ml of a toluene solution containing 22.5 g of phosgene over an hour while maintaining the reaction temperature at 0°-5° C. After stirring at this temperature for an hour, the temperature of the reaction mixture was raised to the room temperature and excess phosgene was purged with nitrogen. The precipitated crystals were filtered off. The toluene layer was separated from the filtrate and dried. Toluene was distilled off under reduced pressure. The resulting residue was vacuum distilled to obtain 11.38 g of desired 4-methyl-o-phenylenecarbonate as colorless oil having a boiling point of 74° C./3 mmHg.

Elementary Analysis [C$_8$H$_6$O$_3$]:

|  | C | H |
| --- | --- | --- |
| Calculated (%) | 64.00 | 4.03 |
| Found (%) | 63.80 | 4.13 |

What is claimed is:

1. A method of inducing the production and secretion of nerve growth factor, comprising administering to a person in need thereof an amount of a compound of the formula

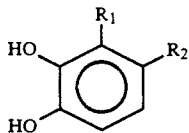

wherein $R_1$ and $R_2$ are each, independently, a hydrogen atom or a lower alkyl group, sufficient to induce the production and secretion of nerve growth factor, wherein said administering is by oral administration.

2. A method of inducing the production and secretion of nerve growth factor, comprising administering to a person in need thereof an amount of a compound of the formula

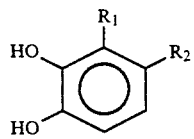

wherein $R_1$ and $R_2$ are each, independently, a hydrogen atom or a lower alkyl group, sufficient to induce the production and secretion of nerve growth factor, wherein said administering is by suppository, injection of infusion.

3. A method of inducing the production and secretion of nerve growth factor, comprising administering to a person in need thereof an amount of a compound of the formula

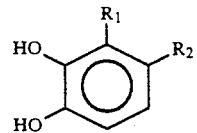

sufficient to induce the production and secretion of nerve growth factor, wherein one of $R_1$ and $R_2$ is methyl, ethyl, propyl, butyl or pentyl.

4. A method of inducing the production and secretion of nerve growth factor, comprising administering to a person in need thereof, an amount of a compound of the formula

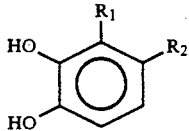

sufficient to induce the production and secretion of nerve growth factor, wherein $R_1$ is H and $R_2$ is methyl, ethyl, propyl, butyl or pentyl.

5. A method of inducing the production and secretion of nerve growth factor, comprising administering to a person in need thereof, an amount of a compound of the formula

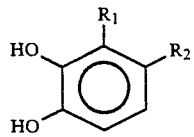

sufficient to induce the production and secretion of nerve growth factor, wherein $R_2$ is H and $R_1$ is methyl, ethyl, propyl, butyl or pentyl.

6. A method of inducing the production and secretion of nerve growth factor, comprising administering to a person in need thereof, a compound of the formula

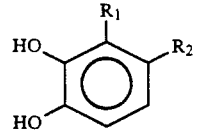

wherein $R_1$ and $R_2$ are each, independently, a hydrogen atom or a lower alkyl group administered at a dosage of 50 to 500 ml per day.

* * * * *